US007636601B2

(12) United States Patent
Overhauser

(10) Patent No.: US 7,636,601 B2
(45) Date of Patent: Dec. 22, 2009

(54) REMOTE CONTROL WITH VOICE DISABLER

(76) Inventor: William W. H. Overhauser, 479 Sycamore Ct., Greenfield, IN (US) 46140

( * ) Notice: Subject to any disclaimer, the term of this patent is extended or adjusted under 35 U.S.C. 154(b) by 651 days.

(21) Appl. No.: 11/600,970

(22) Filed: May 9, 2006

(65) Prior Publication Data

US 2007/0265676 A1 Nov. 15, 2007

(51) Int. Cl.
*A61N 1/18* (2006.01)
(52) U.S. Cl. ...................................................... 607/45
(58) Field of Classification Search .................... 607/45
See application file for complete search history.

(56) References Cited

U.S. PATENT DOCUMENTS

| | | | | | |
|---|---|---|---|---|---|
| 5,193,539 | A | * | 3/1993 | Schulman et al. | 607/61 |
| 5,193,540 | A | * | 3/1993 | Schulman et al. | 607/61 |
| 5,312,439 | A | * | 5/1994 | Loeb | 607/2 |
| 5,324,316 | A | * | 6/1994 | Schulman et al. | 607/61 |
| 5,405,367 | A | * | 4/1995 | Schulman et al. | 607/61 |
| 6,051,017 | A | * | 4/2000 | Loeb et al. | 607/1 |
| 2002/0013612 | A1 | * | 1/2002 | Whitehurst | 607/45 |

* cited by examiner

*Primary Examiner*—Carl H Layno
*Assistant Examiner*—Yun Haeng Lee

(57) ABSTRACT

System and method for temporary disabling the vocal faculties of a person. A voice disabler is implanted between the skull and the anterior occipital lobe of a human subject. The disabler has positive and negative electrodes exposed to the exterior of a bio-proof, non-toxic casing, such that the electrodes interface with the occipital lobe. The casing includes a battery and a switching circuit for applying an electrical charge to the electrodes of a predetermined duration and voltage. The switching circuit is responsive to the detection of radiofrequency triggering signal emitted by an extra-body remote control.

2 Claims, 2 Drawing Sheets

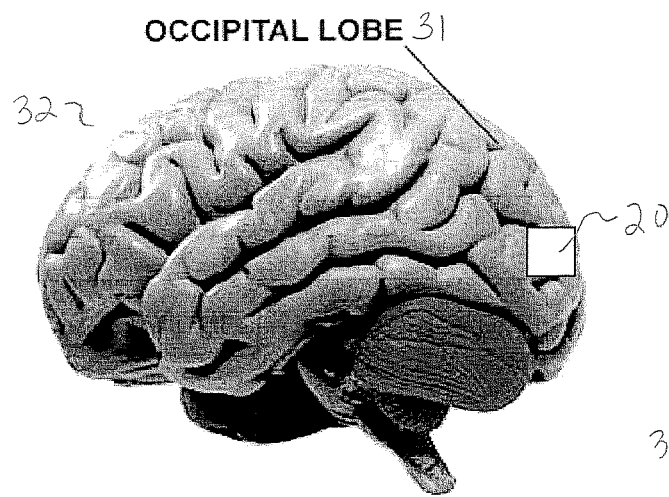
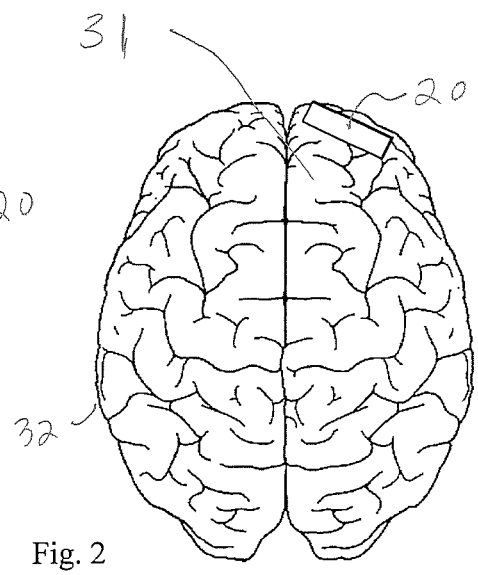
Fig. 1
Fig. 2
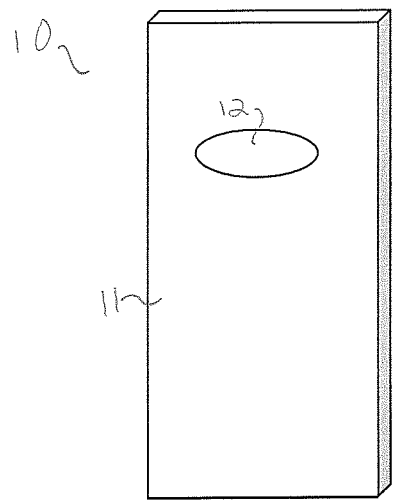
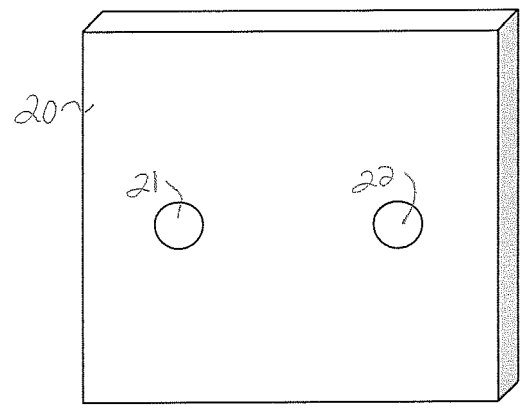
Fig. 3
Fig. 4

REMOTE CONTROL WITH VOICE DISABLER

TECHNICAL FIELD

The present invention relates command and control systems, and in particular to such systems adapted for use within a living body.

BACKGROUND OF THE INVENTION

Remote controls have been designed for a variety of purposes, such as televisions, garage door openers, and even beds. In addition, various electrical devices have been designed for intrabody implantation, such as insulin pumps. Some of these devices, like pacemakers, emit electrical charges to the body. However, pacemakers are designed to apply periodic electrical charges according to a predetermined schedule, such as one discharge per second, in order to stimulate cardiac tissue. Those skilled in the art are also aware of defibrillators which are activated by a person other than the human to which they are applied. However, defibrillators require direct contact by an operator in immediate proximity to the person to which they are applied, and also require careful placement on the appropriate parts of the chest. Hence, defibrillators are not conducive to remote control operation by another person.

The need to incapacitate the vocal capacity of persons is well documented but has heretofore not been capable of a sound solution. Persons in need of the application of such a function include mentally impaired persons who are sometimes inclined to make sudden, loud and disruptive utterances. Also, Tourette's syndrome is a common childhood-onset condition. It can be associated with features of many other conditions. Tourette's syndrome is a neurological or neurochemical disorder characterized by tics. These tics are involuntary, rapid, sudden movements or vocalization that occurs repeatedly in the same way. Symptoms of Tourette's syndrome include multiple motor and one or more vocal tics present at some time during the disorder. More severe cases can inhibit or prevent the individual from engaging in common activities. In addition, the occasional sibling could benefit from temporary devocalization in order in enhance peace and tranquility among family members and others in their presence.

Various techniques for disabling the voice of a person are also known in the art. For example, gagging or chocking a person can temporarily disable a person's vocal faculties, but such methods are undesirable as they can be violent or lead to inadvertent or intentional injury. Another technique is surgical removal of the vocal cords, but such a technique is permanent and is therefore suboptimal. While loud music or other sounds could be played in order to drown out the undesired words or sounds of a person, this solution has the disadvantage of being too loud.

It is also known in the art to limit perception of the vocalizations of others via electronic equipment such as noise-canceling headphones. However, noise canceling headphones must be individually worn by each person within hearing range of the person whose voice it is desired not to hear, which can significantly increase the cost of this solution. In addition, noise canceling headphones do not operate to limit the vocalizations at their source, which is an important design constraint in the present field of art.

Accordingly, it is desirable to provide a system and method for temporarily disabling the vocal capacity of a person that is non-violent and which can be actuated upon demand by another person. It is also desirable to provide a system in which such result may be accomplished when not in immediate physical proximity to the persons whose voice is to be disabled so as to minimize the success of any retaliatory violence.

SUMMARY OF THE INVENTION

A remote control is adapted to actuate a voice disabler is implanted between the skull and the anterior occipital lobe of a human subject. The disabler has positive and negative electrodes exposed to the exterior of a bio-proof, non-toxic casing, such that the electrodes interface with the occipital lobe. The casing includes a battery and a switching circuit for applying an electrical charge to the electrodes of a predetermined duration and voltage. The switching circuit is responsive to the detection of radiofrequency triggering signal emitted by an extra-body remote control.

BRIEF DESCRIPTION OF THE DRAWINGS

FIG. 1 is a side view of a human brain showing placement of the disabler of the invention on the occipital lobe of the brain.

FIG. 2 is a top view of a human brain showing placement of the disabler of the invention on the occipital lobe of the brain.

FIG. 3 is a perspective view of a remote control of the invention.

FIG. 4 is a perspective view of the vocal disabler of the present invention showing the exposed electrodes.

DETAILED DESCRIPTION OF THE PREFERRED EMBODIMENTS

Figure 5:
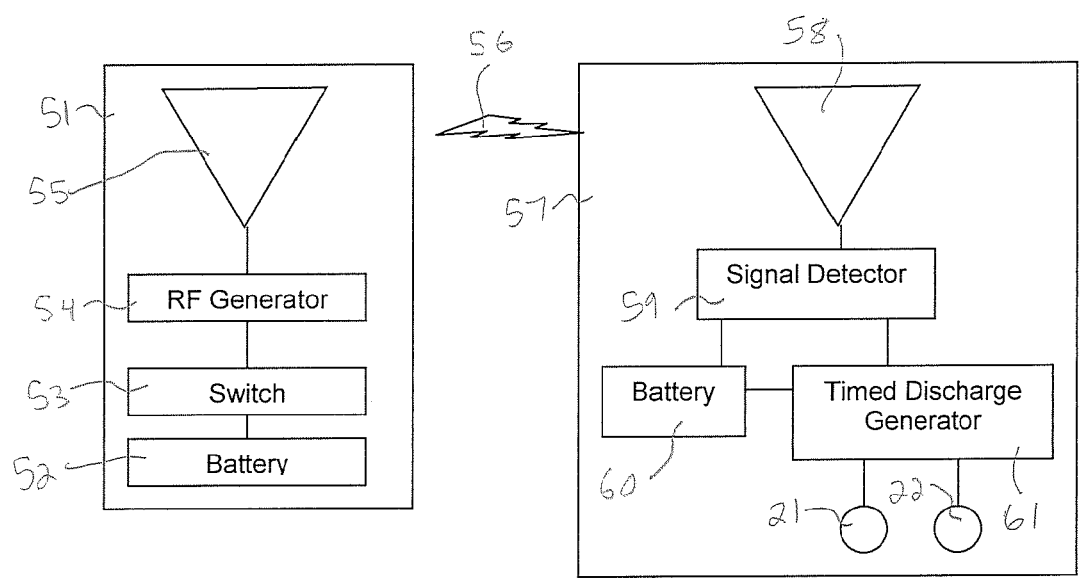
FIG. 5 is a schematic diagram of the remote control and vocal disabler units in accordance with the present invention.

As shown in FIG. 3 remote control 10 comprises an exterior housing 11 and an actuator button 12. The button is depressible, and thereupon generates a triggering signal, at a frequency such 40.685 MHz. The triggering should have an effective transmission distance of at least 100 feet. The remote control unit is of an extra-body design, and comprises a replaceable battery power source within.

FIG. 4 is a perspective view of the vocal disabler unit of the present invention. The disabler is characterized by casing 20 and positive electrode 21 and negative electrode 22. The casing is preferably comprised of a bio-proof, non-toxic material such as titanium. Electrodes 21 and 22 have a substantially circular exposed surface are for interfacing with the occipital lobe of a human subject, as shown in FIGS. 1 and 2. Casing 20 has sealed therein other electronic components, preferably by an epoxy resin to reduce bio-interference with or bio-corrosion of the components within the disabler unit.

As shown if FIGS. 1 and 2, the vocal disabler unit should be positioned beneath the skull of a human subject so that electrodes 21 and 22 interface and engage the occipital lobe 31 of brain 32 of the human subject. Such positioned is normally accomplished via a surgical procedure requiring an incision of the skin and sawing of a flap in the skull so the disabler unit may be placed beneath the flap. Of course, after the vocal disabler unit has been correctly positioned against the occidental lobe, the flap should be returned to its original position and the incision should be sewn to prevent the human subject from bleeding to death or otherwise suffering from adverse medical complications.

FIG. 5 is a schematic diagram of the remote control and vocal disabler units in accordance with the present invention.

Remote control unit 51 includes replaceable battery 52, depressible switch 53, RF Generator 54 and transmitting antenna 55. When depressible switch 53 is depressed, the electrical circuit is completed thereby causing RF generator to generate a triggering signal 56 which is transmitted through antenna 55.

Triggering signal 56 is received by antenna 58 of disabler unit 57, and provided to signal detector 59. In response to a detected signal, signal generator 59 activates times discharge generator 61 which provide an electrical charge to electrodes 21 and 22. Electrodes 21 and 22, having been implanted in the human subject, discharge the electrical charge to the occipital lobe, to thereby disable the vocal faculties of the human subject. In one embodiment, the electrical discharge is between 4-10 volts, preferably 7 volts, and has a duration of seven seconds.

The operable components of vocal disabler are powered by lithium iodine battery 60, which can be selected useful life of approximately ten years.

Those of skill in the art will appreciate the system described herein achieves the desired purpose of limiting or disabling the vocal capabilities of the person while allowing convenient remote control by another person.

I claim:

1. A remote controlled voice disabler, comprising:

An extra-body remote control, comprising a replaceable battery power source, a push button operable to emit a triggering radio frequency signal detectable by a switching circuit of a vocal disabler unit;

the triggering radio frequency signal being approximately 40.685 MHz in frequency, and having a transmission distance of at least 100 feet; and;

a vocal disabler unit adapted to be implanted between the skull and the anterior occipital lobe of a human subject, comprising flat positive and negative electrodes exposed to the exterior of a bio-proof, non-toxic titanium casing, such that the electrodes interface with the anterior occipital lobe, the casing having a rectangular prismatic shape with an anterior occipital lobe engaging side and an opposing skull engaging side substantially co-planar with the anterior occipital lobe engaging side; the electrodes having a substantially circular surface area for interfacing with the anterior occipital lobe, thereby forming a portion of, and being flush with, the anterior occipital lobe engaging side; and the casing comprising a lithium iodine battery and containing therein a timed discharge generator for applying a vocalization disabling electrical charge of at least seven seconds in duration and between 4 to 10 volts in magnitude to the electrodes, the timed discharge generator being responsive to the detection of the radiofrequency triggering signal emitted by the extra-body remote control; the timed discharge generator being sealed within the casing by an epoxy resin;

whereby the electrical charge of the voice disabler unit is operable to temporarily disable the vocal faculties of the human subject.

2. A method of temporarily disabling the vocal faculties of a person, comprising the steps of:

providing the extra-body remote control of claim 1 and the vocal disabler unit of claim 1; and implanting in the vocal disabler within the skull of a person so that anterior occipital lobe engaging side of the casing and the circular electrodes interface with the anterior occipital lobe of the person and the opposing skull engaging side interfaces with the skull of the person;

depressing the push button of the extra-body remote control to thereby cause emission of a triggering radio frequency signal;

detecting the triggering radio frequency signal using the vocal disabler unit;

discharging from the vocal disabling unit a vocalization disabling electrical charge of at least seven seconds in duration and between 4 to 10 volts in magnitude to the electrodes so that the charge is transmitted to the anterior occipital lobe of the person to thereby disable the person's vocal faculties.

* * * * *